United States Patent
Allen et al.

(10) Patent No.: US 10,387,793 B2
(45) Date of Patent: Aug. 20, 2019

(54) AUTOMATIC GENERATION OF TRAINING CASES AND ANSWER KEY FROM HISTORICAL CORPUS

(71) Applicant: International Business Machines Corporation, Armonk, NY (US)

(72) Inventors: Corville O. Allen, Morrisville, NC (US); Christine A. Grev, Rochester, MN (US); Richard J. Stevens, Monkton, VT (US); Kathryn L. Whaley, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 886 days.

(21) Appl. No.: 14/552,948

(22) Filed: Nov. 25, 2014

(65) Prior Publication Data
US 2016/0148114 A1   May 26, 2016

(51) Int. Cl.
G06N 20/00 (2019.01)
G16H 10/60 (2018.01)
G06F 19/00 (2018.01)

(52) U.S. Cl.
CPC .......... *G06N 20/00* (2019.01); *G06F 19/00* (2013.01); *G16H 10/60* (2018.01)

(58) Field of Classification Search
CPC .................. G06N 99/005; G16H 10/60
See application file for complete search history.

(56) References Cited

U.S. PATENT DOCUMENTS

| | | |
|---|---|---|
| 7,603,330 B2 | 10/2009 | Gupta et al. |
| 8,340,955 B2 | 12/2012 | Brown et al. |
| 8,473,499 B2 | 6/2013 | Song et al. |
| 8,543,565 B2 | 9/2013 | Feng |
| 8,738,617 B2 | 5/2014 | Brown et al. |
| 8,805,756 B2 | 8/2014 | Boss et al. |
| 8,819,007 B2 | 8/2014 | Brown et al. |
| 2009/0287678 A1 | 11/2009 | Brown et al. |

(Continued)

OTHER PUBLICATIONS

Ferrucci, David, et al. "Building Watson: An overview of the DeepQA project." AI magazine 31.3 (2010): 59-79.*

(Continued)

*Primary Examiner* — Scott A. Waldron
*Assistant Examiner* — Kevin W Figueroa
(74) *Attorney, Agent, or Firm* — Stephen J. Walder, Jr.; Diana R. Gerhardt

(57) ABSTRACT

Mechanisms are provided for training and operating a Question and Answer (QA) system pipeline. A corpus of information is received which comprises historical data to which one or more filter criteria are applied to extract filtered historical data relevant to a training objective for training the QA system pipeline. Attribute data, action data, and temporal characteristic data are captured from the filtered historical data. An answer key entry is automatically generated in an automatically generated training answer key data structure based on the attribute data, action data, and temporal characteristic data. The correct answer associated with the answer key entry is an action specified by the action data. The temporal characteristic data provides a historical context for the answer key entry. The QA system pipeline is trained using the automatically generated training answer key data structure.

20 Claims, 7 Drawing Sheets

(56) References Cited

U.S. PATENT DOCUMENTS

| | | |
|---|---|---|
| 2010/0063797 A1 | 3/2010 | Cong et al. |
| 2011/0066587 A1 | 3/2011 | Ferrucci et al. |
| 2011/0125734 A1 | 5/2011 | Duboue et al. |
| 2011/0125783 A1* | 5/2011 | Whale ............... G06F 17/30029 707/769 |
| 2011/0258002 A1* | 10/2011 | Green, III ............. G06F 19/322 705/3 |
| 2012/0077178 A1* | 3/2012 | Bagchi .................... G09B 7/00 434/362 |
| 2013/0007055 A1 | 1/2013 | Brown et al. |
| 2013/0017523 A1* | 1/2013 | Barborak ................. G09B 7/04 434/322 |
| 2013/0018652 A1 | 1/2013 | Ferrucci et al. |
| 2013/0066886 A1 | 3/2013 | Bagchi et al. |
| 2013/0304672 A1* | 11/2013 | Varma .................... G06Q 40/06 705/36 R |
| 2014/0006012 A1 | 1/2014 | Zhou et al. |
| 2014/0172757 A1 | 6/2014 | Liu |
| 2014/0172883 A1 | 6/2014 | Clark et al. |
| 2014/0272884 A1 | 9/2014 | Allen et al. |
| 2014/0280087 A1 | 9/2014 | Isensee et al. |
| 2014/0297571 A1 | 10/2014 | Beamon et al. |
| 2014/0298199 A1 | 10/2014 | Johnson, Jr. et al. |

OTHER PUBLICATIONS

High, Rob, "The Era of Cognitive Systems: An Inside Look at IBM Watson and How it Works", IBM Corporation, Redbooks, Dec. 12, 2012, 16 pages.

Yuan, Michael J., "Watson and healthcare, How natural language processing and semantic search could revolutionize clinical decision support", IBM developerWorks, IBM Corporation, Apr. 12, 2011, 14 pages.

* cited by examiner

AUTOMATIC GENERATION OF TRAINING CASES AND ANSWER KEY FROM HISTORICAL CORPUS

BACKGROUND

The present application relates generally to an improved data processing apparatus and method and more specifically to mechanisms for automatically generating training cases and answer keys from a historical corpus of information.

With the increased usage of computing networks, such as the Internet, humans are currently inundated and overwhelmed with the amount of information available to them from various structured and unstructured sources. However, information gaps abound as users try to piece together what they can find that they believe to be relevant during searches for information on various subjects. To assist with such searches, recent research has been directed to generating Question and Answer (QA) systems which may take an input question, analyze it, and return results indicative of the most probable answer to the input question. QA systems provide automated mechanisms for searching through large sets of sources of content, e.g., electronic documents, and analyze them with regard to an input question to determine an answer to the question and a confidence measure as to how accurate an answer is for answering the input question.

Examples, of QA systems are Siri® from Apple®, Cortana® from Microsoft®, and the IBM Watson™ system available from International Business Machines (IBM®) Corporation of Armonk, New York. The IBM Watson™ system is an application of advanced natural language processing, information retrieval, knowledge representation and reasoning, and machine learning technologies to the field of open domain question answering. The IBM Watson™ system is built on IBM's DeepQA™ technology used for hypothesis generation, massive evidence gathering, analysis, and scoring. DeepQA™ takes an input question, analyzes it, decomposes the question into constituent parts, generates one or more hypothesis based on the decomposed question and results of a primary search of answer sources, performs hypothesis and evidence scoring based on a retrieval of evidence from evidence sources, performs synthesis of the one or more hypothesis, and based on trained models, performs a final merging and ranking to output an answer to the input question along with a confidence measure.

SUMMARY

In one illustrative embodiment, a method, in a data processing system having a processor and a memory configured with logic for implementing a Question and Answer (QA) system pipeline, is provided. The method comprises receiving, by the data processing system, a corpus of information comprising historical data and automatically applying, by the data processing system, one or more filter criteria to the historical data to extract filtered historical data relevant to a training objective for training the QA system pipeline. The method further comprises automatically capturing, by the data processing system, attribute data, action data, and temporal characteristic data from the filtered historical data. Moreover, the method comprises automatically generating, by the data processing system, an answer key entry in an automatically generated training answer key data structure based on the attribute data, action data, and temporal characteristic data. The correct answer associated with the answer key entry is an action specified by the action data. The temporal characteristic data provides a historical context for the answer key entry. In addition, the method comprises training, by the data processing system, the QA system pipeline using the automatically generated training answer key data structure.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
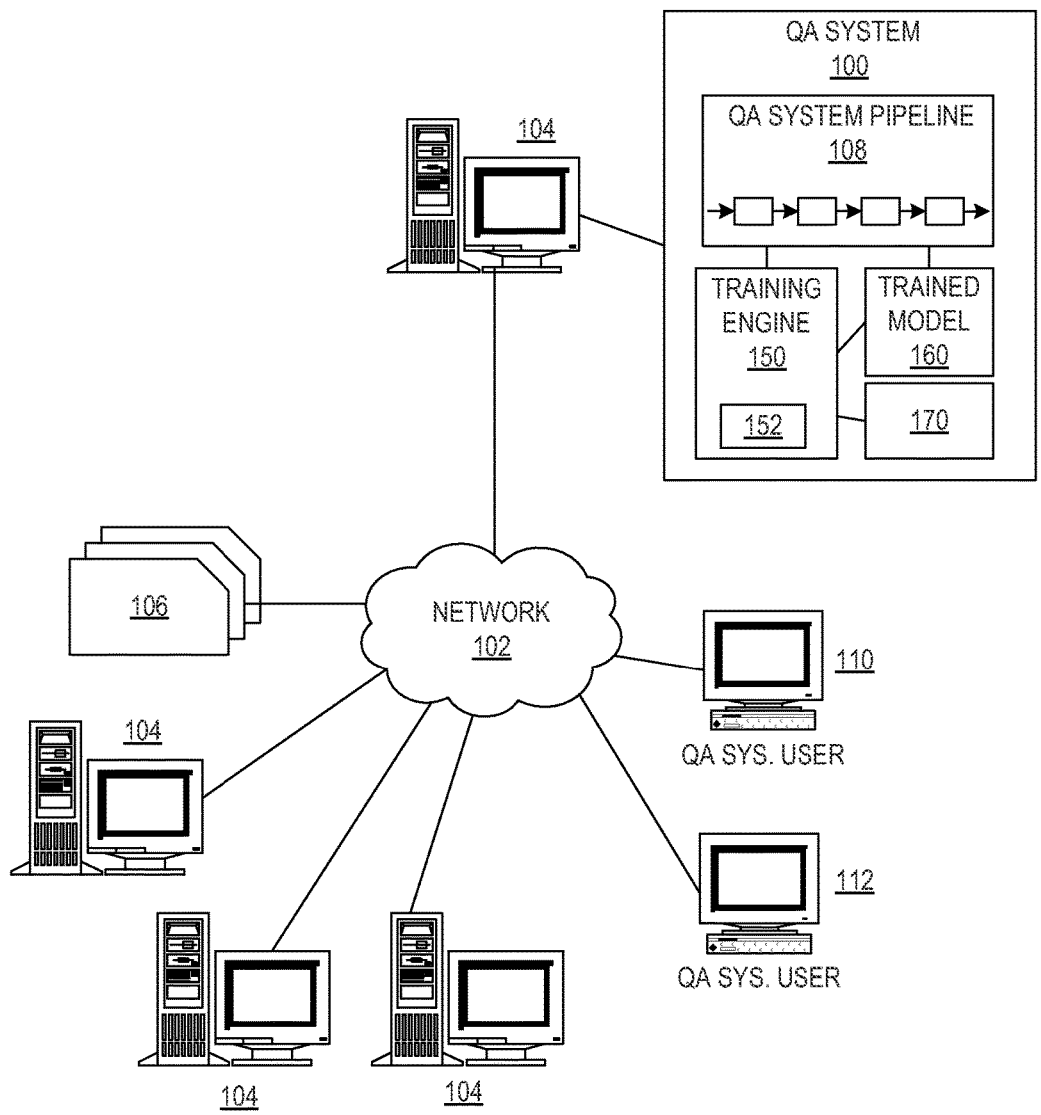
FIG. 1 depicts a schematic diagram of one illustrative embodiment of a question/answer creation (QA) system in a computer network.

One area where Question and Answer (QA) systems, such as the IBM Watson™ QA system, available from International Business Machines (IBM) Corporation of Armonk, New York, are being applied is to the area of healthcare. QA systems may be able to assist patients, doctors, nurses, paramedics, medical technicians, and other healthcare workers in evaluating and treating patients for various maladies. However, such QA systems require training using training sets of data, training sets of questions (where the training sets of data and training sets of questions together are referred to as "training cases"), and answer keys to ensure that the QA system logic itself is operating property and can be applied to new data and process new questions correctly. This presents a problem in areas where the corpus of data upon which the QA system operates changes considerably over time and where new knowledge is obtained on a regular basis which will invalidate or modify answers to the same question over time.

For example, in the healthcare industry, data in patient records continues to increase over time as the patient's treatments and care by the patient's various physicians continues. Thus, if a QA system is trained on a corpus of data including the patient's medical file at time T1, the information available to the QA system at time T1 will be different than the information available to the QA system at a later time T2. For example, at time T1 the patient's diagnosis may have been a particular malady and a treatment may have been administered and at a later time T2 it is discovered that the treatment did not result in the patient being cured. If only the information at the later time T2 is considered, then the diagnosis of the patient may have been considered to be incorrect even though at the time T1 the diagnosis may have been correct based on the information known at the time.

Similarly, in the healthcare industry, new discoveries are being made on a regular basis which may change or invalidate previous treatments or patient recommendations that, at a previous time, were considered to be the correct treatments or recommendations. That is, as understanding of an area increases, previous conclusions based on a different set of knowledge may become obsolete. In the context of a QA system, this may lead to a QA system that was trained on a previous training data set and/or previous answer key giving incorrect answers to questions at a later time when the corpus of data, representing current knowledge in a particular domain, has expanded and answers to training questions have changed over time. However, at the time that the QA system was trained, the answers generated (which are now obsolete) may have been the correct answers for the knowledge at the time.

The historical time periods of test cases, i.e. test questions and corresponding corpus of information, and corresponding answer keys is especially important when training a QA system on such historical data. That is, if one is training a QA system to generate an answer A from the answer key, given a question or set of question features Q, it is important to know the historical context of when the answer A was determined to be the correct answer for the question Q and take into consideration only the knowledge in the corpus of information that was available at the time T1 when the answer A was determined to be the correct answer for the question Q. As an example, if a patient's medical record indicates that the patient came in on January $5^{th}$ complaining of a runny nose, sore throat, and a fever and the doctor diagnosed the patient as having the flu and prescribed a medication, e.g., Tamiflu, then on January $5^{th}$ the correct answer to the question of how to treat the patient's malady was to prescribe Tamiflu. However, later the patient's medical record may indicate that the patient returned on January $20^{th}$ complaining of additional symptoms such as red eyes, a raised rash, chest pain, stomach pain, bleeding from the eyes, etc., and the diagnosis was much more severe, e.g., Ebola hemorrhagic fever, which results in a different treatment plan.

If the QA system is being trained on January $15^{th}$ using patient medical record data including this patient's medical record, the runny nose, sore throat, and fever may be associated with flu in the answer key when training the QA system. However, when the QA system is run on test questions after January 20th, if the full set of medical record data is used when processing questions by the QA system, then the QA system may generate an answer of a diagnosis of Ebola with a corresponding treatment. Comparing this answer to the answer key may result in the QA system's result being determined to be incorrect. If the later obtained patient medical record data were not included in the evaluation of the question, then the correct answer of a diagnosis of the flu and a treatment of Tamiflu may be generated.

Moreover, it is often time consuming and expensive to create answer keys for training QA systems. Typically, the creation of answer keys for training QA systems is a manual process involving many hours of Subject Matter Expert (SME) time to generate a large enough set of answer key entries to adequately train a QA system to perform properly based on a training corpus of data. Each entry in the answer key, also referred to as a "ground truth" or "golden" set of data, represents a question (or set of question features for a particular question) and a corresponding correct answer that should be returned by the QA system, operating on a training corpus of data, assuming proper operation of the QA system. When training the QA system, the question is submitted to the QA system for processing, which includes executing queries against a training corpus of data, and candidate answers are returned from which a final answer is selected by the QA system. The final answer is compared to the correct answer in the answer key to determine if the QA system has processed the question correctly or not. Based on any differences between the final answer generated by the QA system and the correct answer in the answer key, the operation of the QA system logic may be adjusted so as to improve its operation and likelihood of generating the correct answer. It can be appreciated that to fully exercise and train the QA system, a large number of such training questions must be submitted to the QA system so that the various possible types of questions that may be answered by the QA system may be characterized during the training This requires a SME to manually generate a large number of such training question and answer key entries.

Moreover, it should be noted that these manually generated training question and corresponding answer key entries (also referred to as "training cases") may become obsolete over time and in need of reproduction, e.g., there may be new tests invented over time that expand the set of information available with the "question" and/or there may be new therapies available that would serve as superior answers to the question. Thus, a system which is able to automate the process of answer key/training data generation can better cope with the continuous advancement of knowledge in a given field.

The illustrative embodiments provide mechanisms for automatically generating answer keys and training questions (i.e. test cases) for training a QA system based on historical data in a corpus of information. With these mechanisms, historical data of a corpus of information, including both structured (e.g., designated fields in a form) and unstructured data content (e.g., natural language statements), is read and processed. The historical data is filtered based on training objectives which specify one or more filter criteria to be applied to the historical data in the corpus so as to generate a filtered corpus of information (or training corpus) upon which training is to be performed. These filter criteria may take many different forms. For example, one filter criterion may be to select historical data associated with specific sources of data in the corpus or specific types of sources of data in the corpus. Another filter criterion may be to select historical data that is more contemporary, i.e. not older than a particular time period. Another filter criterion may be to select historical data with a particular level of confidence associated with the data.

For example, in one illustrative embodiment, the corpus of information comprises patient medical records comprising historical medical data for various patients treated by medical personnel. Each patient medical record may have structured and/or unstructured entries that specify symptoms, complaints, demographic information, laboratory results information, and the like, in association with diagnosis information, therapy and treatment prescriptions, results information, information about the medical professional providing care, and the like. In applying the first filter criteria based on source of information, the source(s) that the QA system is intended to emulate may be selected as the filter criteria for the patient medical records. For example, if the QA system is intended to emulate a doctor or attending physician, then the patient medical records in the corpus may be filtered to extract information associated with entries in the patient medical records that are associated with doctors or attending physicians. These individuals are considered virtual subject matter experts (SMEs) and are providing training answer key information automatically through the extraction of the information that they have entered into the patient medical records and using that information as a basis for creating the training answer key. Such filtering of information based on source, and in the specific case of a type of medical professional or a specific medical professional, may be used in cases where the goal is to train the QA system to emulate a type of medical professional when answering questions, e.g., oncology doctors, established doctor versus a first year resident, etc., or a specific medical professional, e.g., Dr. Smith and Johns Hopkins.

In applying the second filter criterion mentioned above, temporal characteristics of the data in the patient medical records may be compared to a current date/time, and one or more selection thresholds, so as to select a sub-portion of the patient medical records to be used to generate the training answer key. The thresholds may be set so as to specify the historical time frame of interest for training the QA system, e.g., only the most contemporary data is utilized. For example, if one knows that a particular area of medical technology tends to have significant advancements every two years or so, then a threshold of two years prior to the current date/time may be established and used to compare against entries in the patient medical records such that entries older than two years will be effectively filtered out of the resulting data used to generate the training answer key. This avoids data that was created prior to the most recent advancements from being considered when generating the training answer key.

With regard to the application of the third criterion above, entries in medical records that have result information indicative of a positive result may be selected from the patient medical records, e.g., the patient is cured, the patient indicates a reduction in symptoms, the doctor indicates responsiveness to the treatment or therapy, or the like. In this way, correct diagnosis information, therapies, treatments, and the like that lead to patients being properly diagnosed, cured or positively affected by the therapies, treatments, and the like are identified and used as a basis for generating an answer key and training a QA system.

The historical data in the corpus of information may be processed iteratively and relevant attributes, actions taken, and temporal characteristics in the historical data of the resulting training corpus may be captured and stored. These attributes, actions, and temporal characteristics may then be used to generate a new training answer key. For this new training answer key, the correct answer is the action taken within the historical data instance represented by the temporal characteristic. For example, for a particular patient medical record, the relevant attributes may be symptoms and a diagnosis, the actions taken may be a therapy or treatment, and the temporal characteristics may be a particular date on which the therapy or treatment was prescribed.

Having generated a training answer key from historical data, where entries in the training answer key include temporal characteristics of the corresponding entry, the training answer key is utilized with training cases to train the QA system using historically derived training data. The training answer key specifies question features, e.g., patient attributes including symptoms, complaints, physical condition indicators (blood pressure, temperature, and the like), an answer (e.g., diagnosis, treatment, therapy, and/or the like), and a historical temporal characteristic indicative of the historical date/time at which the answer was considered correct for the particular question features.

Training cases, each comprising a question having question features and a reference temporal characteristic for the training case, are submitted to the QA system pipeline for processing. The QA system pipeline performs operations for parsing and performing natural language processing of the question and/or question features to generate queries to be applied to a training corpus of information (e.g., a training set of patient medical records and supporting evidence/literature). When processing the training case, the training corpus of information may be filtered based on the reference temporal characteristic of the training case being processed such that a sub-corpus having only the information that existed at the time of the reference temporal characteristic or before are included in the sub-corpus. Thus, the QA system pipeline processes the training case based on a sub-corpus that corresponds to the reference temporal characteristic of the training case to generate one or more candidate answers and corresponding confidence scores for the training case. The one or more candidate answers and corresponding confidence scores may be used to generate a final answer for the training case.

The final answer for the training case is output to a machine learning engine which receives the final answer and corresponding confidence score information and compares it to a corresponding correct answer in the training answer key for the same training case attributes and reference temporal characteristic. Based on the comparison, a trained model is generated. The trained model is a statistical model reflecting how various answer scoring algorithms employed within the QA pipeline should be weighted to yield optimal results/accuracy based on the set of training cases used for training The trained model is used by the QA pipeline at runtime to evaluate new cases presented to the QA pipeline based on the trained model having been trained using the training cases and training answer key. Candidate answers for new cases are evaluated by first running the QA pipeline answer scoring algorithms and then applying the weighting factors from the machine learning-derived model, i.e. the trained model, to yield an overall confidence level for each candidate answer. Thus, the trained model is generated while the QA system pipeline is operated in a special "training" mode using the automatically generated training cases and training answer key to produce a trained, machine learning-based model that is then used with the same QA system pipeline when it is operating in a non-training runtime mode.

It should be appreciated that while the illustrative embodiments described herein will be described in the context of a healthcare or medical domain with the corpus of information comprising patient medical records and supporting medical evidence/literature, the illustrative embodiments are not limited to the healthcare or medical domains. To the contrary, the mechanisms of the illustrative embodiments may be applied to any domain in which a corpus of information may be analyzed automatically to extract answer key information for generating a training answer key and in which training cases specifying a question or question attributes and a reference temporal characteristic may be automatically generated from the corpus of information. Thus, the mechanisms of the illustrative embodiments may be applied to legal domains, business account and/or policy domains, financial investment domains, or any other domain deemed appropriate in view of the present description.

For example, with regard to the financial investment domain, the QA system may be trained using the mechanisms of the illustrative embodiments to emulate an expert investor that evaluates a set investors and their decisions regarding financial performance attributes across a set of companies or financial instruments. The QA system may be trained by the mechanisms of the illustrative embodiments based on historical decisions (correct answers) made by such expert investors, considering a corpus of financial performance information, at the time an investment was made. Moreover, the training may select historical data for just those investments made by these individuals which lead to a good return (as defined by one or more threshold return values). The application of the mechanisms of the illustrative embodiments to other domains will become apparent to those of ordinary skill in the art in view of the present specification.

Before beginning a more detailed discussion of the various aspects of the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
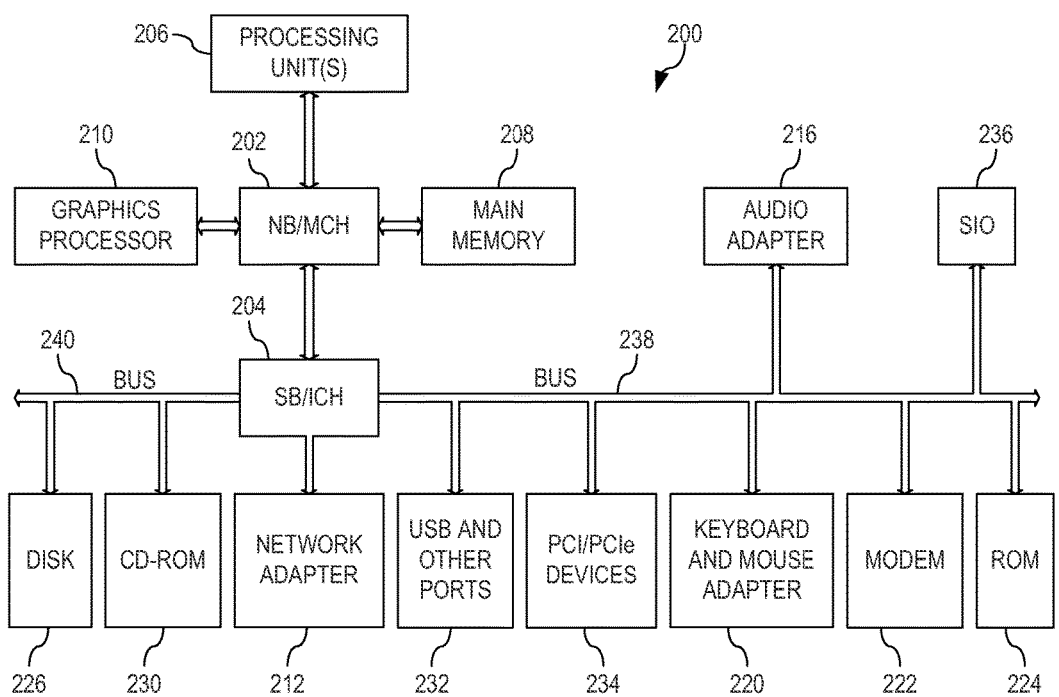
FIG. 2 is a block diagram of an example data processing system in which aspects of the illustrative embodiments are implemented.
Figure 3:
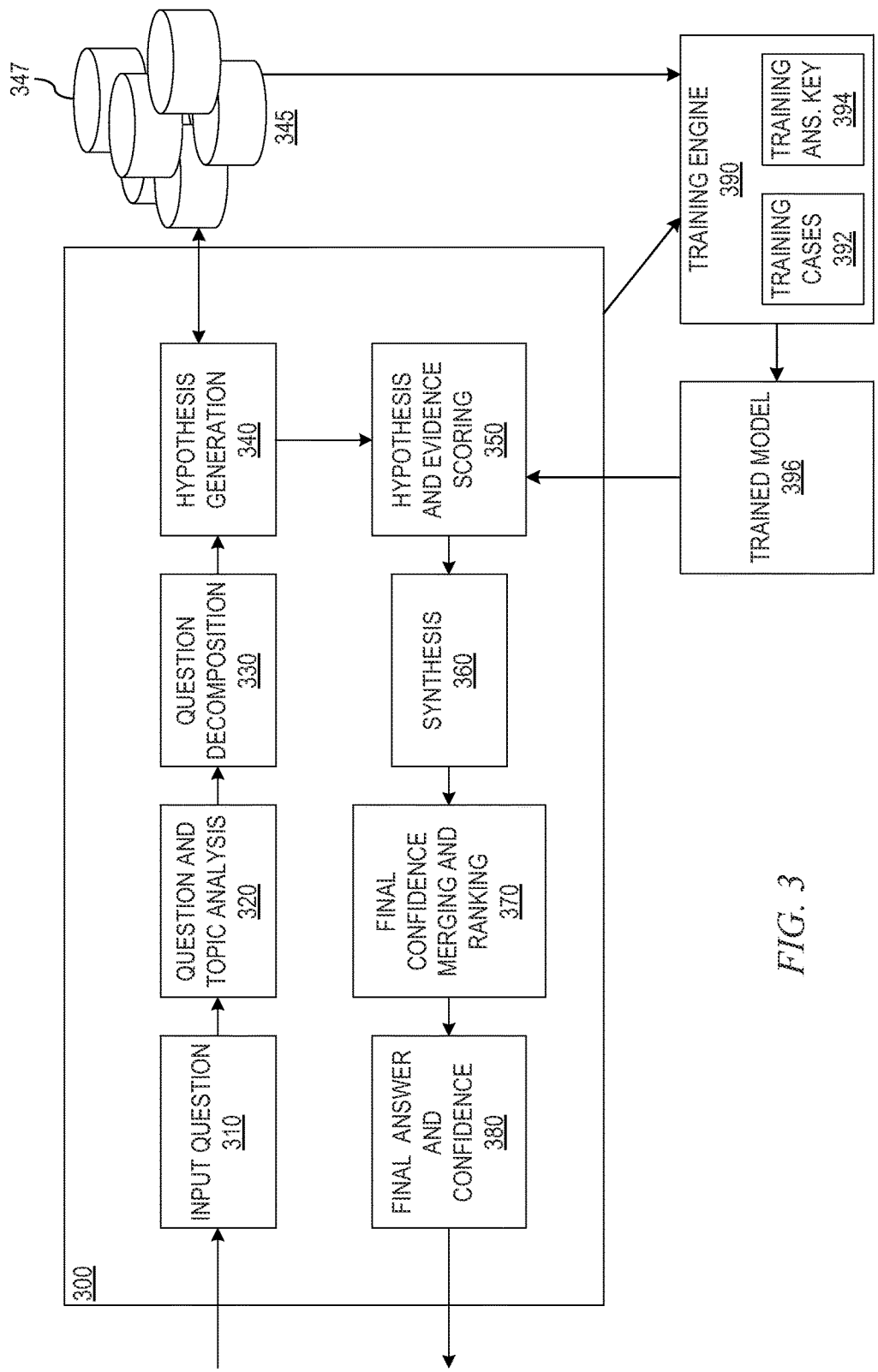
FIG. 3 illustrates a QA system pipeline for processing an input question in accordance with one illustrative embodiment.

Thus, the illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

In particular, FIGS. 1-3 are directed to describing an example Question Answering (QA) system (also referred to as a Question/Answer system or Question and Answer system), methodology, and computer program product with which the mechanisms of the illustrative embodiments are implemented. As will be discussed in greater detail hereafter, the illustrative embodiments are integrated in, augment, and extend the functionality of these QA mechanisms with regard to by providing mechanisms for automatically generating a training answer key and training cases for training the QA system based on historical data in a corpus of information. Moreover, the illustrative embodiments provide mechanisms for filtering the corpus of information used to train the QA system based on temporal characteristics of the training cases so as to reflect only the information available at the particular time when the answer key's determined correct answer was determined. This ensures proper training of the QA system even in situations where the training corpus of information comprises information spanning a large historical time period, some of which was present only after the training case's temporal characteristic. The temporal characteristics will be considered to be dates for purposes of this discussion but it should be appreciated that any temporal characteristic may be utilized including times, days of week, years, and the like, rather than specifically month, day, and year.

Since the mechanisms of the illustrative embodiments extend or enhance the operation of a QA system, it is important to first have an understanding of how question and answer creation in a QA system is implemented before describing how the mechanisms of the illustrative embodiments are integrated in and augment such QA systems. It should be appreciated that the QA mechanisms described in FIGS. 1-3 are only examples and are not intended to state or imply any limitation with regard to the type of QA mechanisms with which the illustrative embodiments are implemented. Many modifications to the example QA system shown in FIGS. 1-3 may be implemented in various embodiments of the present invention without departing from the spirit and scope of the present invention.

As an overview, a Question Answering system (QA system) is an artificial intelligence application executing on data processing hardware that answers questions pertaining to a given subject-matter domain presented in natural language. The QA system receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA system. The document may include any file, text, article, or source of data for use in the QA system. For example, a QA system accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to the QA system which then answers the input questions using the content in the corpus of data by evaluating documents, sections of documents, portions of data in the corpus, or the like. When a process evaluates a given section of a document for semantic content, the process can use a variety of conventions to query such document from the QA system, e.g., sending the query to the QA system as a well-formed question which are then interpreted by the QA system and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA system receives an input question, parses the question to extract the major features of the question, uses the extracted features to formulate queries, and then applies those queries to the corpus of data. Based on the application of the queries to the corpus of data, the QA system generates a set of hypotheses, or candidate answers to the input question, by looking across the corpus of data for portions of the corpus of data that have some potential for containing a valuable response to the input question. The QA system then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA system. The statistical model is used to summarize a level of confidence that the QA system has regarding the evidence that the potential response, i.e. candidate answer, is inferred by the question. This process is repeated for each of the candidate answers until the QA system identifies candidate answers that surface as being significantly stronger than others and thus, generates a final answer, or ranked set of answers, for the input question.

As mentioned above, QA systems and mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA system to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA system. Content creators, automated tools, or the like, annotate or otherwise generate metadata for providing information useable by the QA system to identify these question and answer attributes of the content.

Operating on such content, the QA system generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a question/answer creation (QA) system 100 in a computer network 102. One example of a question/answer generation which may be used in conjunction with the principles described herein is described in U.S. Patent Application Publication No. 2011/0125734, which is herein incorporated by reference in its entirety. The QA system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The QA system 100 and network 102 enables question/answer (QA) generation functionality for one or more QA system users via their respective computing devices 110-112. Other embodiments of the QA system 100 may be used with components, systems, sub-systems, and/or devices other than those that are depicted herein.

The QA system 100 is configured to implement a QA system pipeline 108 that receive inputs from various sources. For example, the QA system 100 receives input from the network 102, a corpus of electronic documents 106, QA system users, and/or other data and other possible sources of input. In one embodiment, some or all of the inputs to the QA system 100 are routed through the network 102. The various computing devices 104 on the network 102 include access points for content creators and QA system users. Some of the computing devices 104 include devices for a database storing the corpus of data 106 (which is shown as a separate entity in FIG. 1 for illustrative purposes only). Portions of the corpus of data 106 may also be provided on one or more other network attached storage devices, in one or more databases, or other computing devices not explicitly shown in FIG. 1. The network 102 includes local network connections and remote connections in various embodiments, such that the QA system 100 may operate in environments of any size, including local and global, e.g., the Internet.

In one embodiment, the content creator creates content in a document of the corpus of data 106 for use as part of a corpus of data with the QA system 100. The document includes any file, text, article, or source of data for use in the QA system 100. QA system users access the QA system 100 via a network connection or an Internet connection to the network 102, and input questions to the QA system 100 that are answered by the content in the corpus of data 106. In one embodiment, the questions are formed using natural language. The QA system 100 parses and interprets the question, and provides a response to the QA system user, e.g., QA system user 110, containing one or more answers to the question. In some embodiments, the QA system 100 provides a response to users in a ranked list of candidate answers while in other illustrative embodiments, the QA system 100 provides a single final answer or a combination of a final answer and ranked listing of other candidate answers.

The QA system 100 implements a QA system pipeline 108 which comprises a plurality of stages for processing an input question and the corpus of data 106. The QA system pipeline 108 generates answers for the input question based on the processing of the input question and the corpus of data 106. The QA system pipeline 108 will be described in greater detail hereafter with regard to FIG. 3.

In some illustrative embodiments, the QA system 100 may be the IBM Watson™ QA system available from International Business Machines Corporation of Armonk, New York, which is augmented with the mechanisms of the illustrative embodiments described hereafter. As outlined previously, the IBM Watson™ QA system receives an input question which it then parses to extract the major features of the question, that in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The IBM Watson™ QA system then performs deep analysis on the language of the input question and the language used in each of the portions of the corpus of data found during the application of the queries using a variety of reasoning algorithms. The scores obtained from the various reasoning algorithms are then weighted against a statistical model that summarizes a level of confidence that the IBM Watson™ QA system has regarding the evidence that the potential response, i.e. candidate answer, is inferred by the question. This process is be repeated for each of the candidate answers to generate ranked listing of candidate answers which may then be presented to the user that submitted the input question, or from which a final answer is selected and presented to the user. More information about the IBM Watson™ QA system may be obtained, for example, from the IBM Corporation website, IBM Redbooks, and the like. For example, information about the IBM Watson™ QA system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As shown in FIG. 1, in accordance with the mechanisms of the illustrative embodiments, the QA system 100 further includes a training engine 150 which operates to generate a trained model 160 through a machine learning process. The trained model 160 is utilized by the QA system pipeline 108 to provide the statistical model used to generate the confidence scores for the candidate answers during runtime operation of the QA system 100. The training engine 150 further comprises an automatic training case and training answer key generation engine 152 which automatically generates training cases and a training answer key based on a training corpus of information 170 having historical data. The details of how the training cases and training answer key are generated based on historical data and then utilized to train the QA system will be described in greater detail hereafter.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a QA system 100 and QA system pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 8®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 illustrates a QA system pipeline for processing an input question in accordance with one illustrative embodiment. The QA system pipeline of FIG. 3 may be implemented, for example, as QA system pipeline 108 of QA system 100 in FIG. 1. It should be appreciated that the stages of the QA system pipeline shown in FIG. 3 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems. The QA system pipeline of FIG. 3 is augmented, for example, in one or more of the stages to implement the improved mechanism of the illustrative embodiments described hereafter, additional stages may be provided to implement the improved mechanism, or separate logic from the pipeline 300 may be provided for interfacing with the pipeline 300 and implementing the improved functionality and operations of the illustrative embodiments.

As shown in FIG. 3, the QA system pipeline 300 comprises a plurality of stages 310-380 through which the QA system operates to analyze an input question and generate a final response. In an initial question input stage 310, the QA system receives an input question that is presented in a natural language format. That is, a user inputs, via a user interface, an input question for which the user wishes to obtain an answer, e.g., "Who are Washington's closest advisors?" In response to receiving the input question, the next stage of the QA system pipeline 300, i.e. the question and topic analysis stage 320, parses the input question using natural language processing (NLP) techniques to extract major features from the input question, and classify the major features according to types, e.g., names, dates, or any of a plethora of other defined topics. For example, in the example question above, the term "who" may be associated with a topic for "persons" indicating that the identity of a person is being sought, "Washington" may be identified as a proper name of a person with which the question is associated, "closest" may be identified as a word indicative of proximity or relationship, and "advisors" may be indicative of a noun or other language topic.

In addition, the extracted major features include key words and phrases classified into question characteristics, such as the focus of the question, the lexical answer type (LAT) of the question, and the like. As referred to herein, a lexical answer type (LAT) is a word in, or a word inferred from, the input question that indicates the type of the answer, independent of assigning semantics to that word. For example, in the question "What maneuver was invented in the 1500s to speed up the game and involves two pieces of the same color?," the LAT is the string "maneuver." The focus of a question is the part of the question that, if replaced by the answer, makes the question a standalone statement. For example, in the question "What drug has been shown to relieve the symptoms of ADD with relatively few side effects?," the focus is " drug" since if this word were replaced with the answer, e.g., the answer "Adderall" can be used to replace the term "drug" to generate the sentence "Adderall has been shown to relieve the symptoms of ADD with relatively few side effects." The focus often, but not always, contains the LAT. On the other hand, in many cases it is not possible to infer a meaningful LAT from the focus.

Referring again to FIG. 3, the identified major features are then used during the question decomposition stage 330 to decompose the question into one or more queries that are applied to the corpora of data/information 345 in order to generate one or more hypotheses. The queries are generated in any known or later developed query language, such as the Structure Query Language (SQL), or the like. The queries are applied to one or more databases storing information about the electronic texts, documents, articles, websites, and the like, that make up the corpora of data/information 345. That is, these various sources themselves, different collections of sources, and the like, represent a different corpus 347 within the corpora 345. There may be different corpora 347 defined for different collections of documents based on various criteria depending upon the particular implementation. For example, different corpora may be established for different topics, subject matter categories, sources of information, or the like. As one example, a first corpus may be associated with healthcare documents while a second corpus may be associated with financial documents. Alternatively, one corpus may be documents published by the U.S. Department of Energy while another corpus may be IBM Redbooks documents. Any collection of content having some similar attribute may be considered to be a corpus 347 within the corpora 345.

The queries are applied to one or more databases storing information about the electronic texts, documents, articles, websites, and the like, that make up the corpus of data/ information, e.g., the corpus of data 106 in FIG. 1. The queries are applied to the corpus of data/information at the hypothesis generation stage 340 to generate results identifying potential hypotheses for answering the input question, which can then be evaluated. That is, the application of the queries results in the extraction of portions of the corpus of data/information matching the criteria of the particular query. These portions of the corpus are then analyzed and used, during the hypothesis generation stage 340, to generate hypotheses for answering the input question. These hypotheses are also referred to herein as "candidate answers" for the input question. For any input question, at this stage 340, there may be hundreds of hypotheses or candidate answers generated that may need to be evaluated.

The QA system pipeline 300, in stage 350, then performs a deep analysis and comparison of the language of the input question and the language of each hypothesis or "candidate answer," as well as performs evidence scoring to evaluate the likelihood that the particular hypothesis is a correct answer for the input question. As mentioned above, this involves using a plurality of reasoning algorithms, each performing a separate type of analysis of the language of the input question and/or content of the corpus that provides evidence in support of, or not in support of, the hypothesis. Each reasoning algorithm generates a score based on the analysis it performs which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed. In generally, however, these algorithms look for particular terms, phrases, or patterns of text that are indicative of terms, phrases, or patterns of interest and determine a degree of matching with higher degrees of matching being given relatively higher scores than lower degrees of matching.

Thus, for example, an algorithm may be configured to look for the exact term from an input question or synonyms to that term in the input question, e.g., the exact term or synonyms for the term "movie," and generate a score based on a frequency of use of these exact terms or synonyms. In such a case, exact matches will be given the highest scores, while synonyms may be given lower scores based on a relative ranking of the synonyms as may be specified by a subject matter expert (person with knowledge of the particular domain and terminology used) or automatically determined from frequency of use of the synonym in the corpus corresponding to the domain. Thus, for example, an exact match of the term "movie" in content of the corpus (also referred to as evidence, or evidence passages) is given a highest score. A synonym of movie, such as "motion picture" may be given a lower score but still higher than a synonym of the type "film" or "moving picture show." Instances of the exact matches and synonyms for each evidence passage may be compiled and used in a quantitative function to generate a score for the degree of matching of the evidence passage to the input question.

Thus, for example, a hypothesis or candidate answer to the input question of "What was the first movie?" is "The Horse in Motion." If the evidence passage contains the statements "The first motion picture ever made was 'The Horse in Motion' in 1878 by Eadweard Muybridge. It was a movie of a horse running," and the algorithm is looking for exact matches or synonyms to the focus of the input question, i.e. "movie," then an exact match of "movie" is found in the second sentence of the evidence passage and a highly scored synonym to "movie," i.e. "motion picture," is found in the first sentence of the evidence passage. This may be combined with further analysis of the evidence passage to identify that the text of the candidate answer is present in the evidence passage as well, i.e. "The Horse in Motion." These factors may be combined to give this evidence passage a relatively high score as supporting evidence for the candidate answer "The Horse in Motion" being a correct answer.

It should be appreciated that this is just one simple example of how scoring can be performed. Many other algorithms of various complexity may be used to generate scores for candidate answers and evidence without departing from the spirit and scope of the present invention.

In the synthesis stage 360, the large number of scores generated by the various reasoning algorithms are synthesized into confidence scores or confidence measures for the various hypotheses. This process involves applying weights to the various scores, where the weights have been determined through training of the statistical model employed by the QA system and/or dynamically updated. For example, the weights for scores generated by algorithms that identify exactly matching terms and synonym may be set relatively higher than other algorithms that are evaluating publication dates for evidence passages. The weights themselves may be specified by subject matter experts or learned through machine learning processes that evaluate the significance of characteristics evidence passages and their relative importance to overall candidate answer generation.

The weighted scores are processed in accordance with a statistical model generated through training of the QA system that identifies a manner by which these scores may be combined to generate a confidence score or measure for the individual hypotheses or candidate answers. This confidence score or measure summarizes the level of confidence that the QA system has about the evidence that the candidate answer is inferred by the input question, i.e. that the candidate answer is the correct answer for the input question.

The resulting confidence scores or measures are processed by a final confidence merging and ranking stage 370 which compares the confidence scores and measures to each other, compares them against predetermined thresholds, or performs any other analysis on the confidence scores to determine which hypotheses/candidate answers are the most likely to be the correct answer to the input question. The hypotheses/candidate answers are ranked according to these comparisons to generate a ranked listing of hypotheses/candidate answers (hereafter simply referred to as "candidate answers"). From the ranked listing of candidate answers, at stage 380, a final answer and confidence score, or final set of candidate answers and confidence scores, are generated and output to the submitter of the original input question via a graphical user interface or other mechanism for outputting information.

As mentioned above, the QA system, and QA system pipeline of FIG. 3, are augmented to implement a training engine 390 which operates to generate a trained model 396, through a machine learning process, which is then utilized by the QA system pipeline 300 to provide a statistical model used to apply weights, such as during the hypothesis and evidence scoring stage 350, to generate the confidence scores for the candidate answers during runtime operation of the QA system pipeline 300. This training engine 390 further operates to automatically generate the training cases 392 and training answer key 394 for use in training the QA system pipeline 300, i.e. generating the trained model 396.

Figure 4:
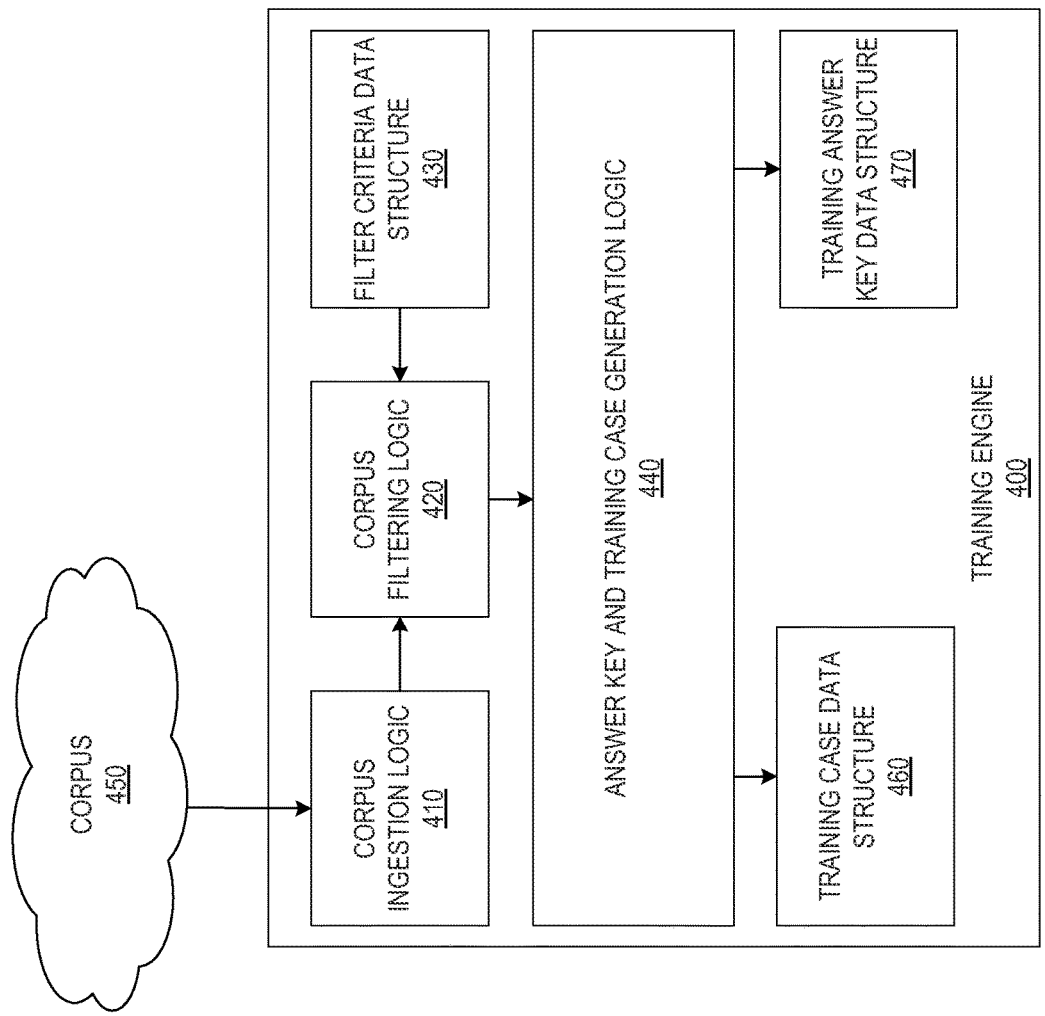
FIG. 4 is an example block diagram of the primary operational elements of a training engine used to generate a training case and answer key in accordance with one illustrative embodiment.

FIG. 4 is an example block diagram of the primary operational elements of a training engine used to generate a training case and answer key in accordance with one illustrative embodiment. As shown in FIG. 4, the training engine 400 comprises corpus ingestion logic 410, corpus filtering logic 420, a filter criteria data structure 430, and answer key and training case generation logic 440. The corpus ingestion logic 410 operates on a training corpus of information 450 to read and process historical data within the corpus of information 450 (both structured and unstructured data), i.e. content within the corpus of information that is associated with dates/times, so as to associate the content with the particular dates/times. This process may involve analyzing the structured content and/or natural language statements within the corpus of information to identify textual patterns of content and structured fields that specify dates/times and then associating the corresponding textual content with those dates/times. Moreover, with regard to unstructured content, a creation date/time of the unstructured content in the corpus may be used to associate a date/time with the unstructured content.

Thus, if the corpus of information 450 comprises patient medical records, for example, structured processing and natural language processing may be applied to the content of a patient medical record to extract those portions of the patient medical record that are associated with dates/times. Hence, entries in the patient medical record that specify previous sessions with the patient to provide health services to the patient, and which have associated dates/times of service of the patient, will be identified and ingested through this process. The ingestion process may extract features from these entries that are recognizable by the corpus ingestion logic 410, e.g., person providing service, patient persona information, symptoms, diagnosis, therapy/treatment, outcome or result, date/time, etc. The extracted features are associated with corresponding annotations specifying the corresponding type of information that is extracted. Thus, for example, if the patient medical record comprises the statement "Jan. 5, 2014: Patient complains of sore throat, runny nose, and fever. Diagnosed patient with the flu and prescribed Tamiflu. Doctor Johnathan Smith" the features extracted may comprise (annotation=value) date=01.05.14 symptom=sore throat, symptom=runny nose, symptom=fever, diagnosis=flu, treatment=Tamiflu, and source=doctor.

The correlation of at least a subset of the extracted features may be stored together as a training case in a training case data structure 460 for further use when training the QA system pipeline. That is, the extracted features representing the features of a question that may be presented to the QA system pipeline may be correlated with the temporal characteristic extracted with the other extracted features to thereby automatically generate a training case having a historical temporal characteristic, referred to as a reference temporal characteristic since it will be used as a reference for filtering the corpus during training as described hereafter. Thus, using the example above, a training case may be of the type:

Symptoms=store throat, runny nose, fever; Date=01.05.14

It should be noted that not all of the extracted features are necessarily utilized in the training case since the training case represents a question that is presented to the QA system. In the case of the QA system pipeline being trained to emulate a doctor and provide medical diagnosis and treatment recommendations, the question is assumed to be a question of "What is the diagnosis and recommended treatment of the patient?" and thus, the extracted features themselves represent the patient context for this question. The answer key and training case generation logic 440 is configured to recognize a particular subset of extracted features as those representing features for specifying a question to the QA system pipeline and thus, this recognized subset of extracted features are compiled and correlated with the extracted temporal characteristic to thereby generate a training case for use in training the QA system.

Filter criteria specified in the filter criteria data structure 430 may be applied to the extracted features of the content of the corpus 440 by the corpus filtering logic 420 to select a subset of the corpus 440 that meets the filter criteria. As mentioned above, examples of filter criteria that may be used to filter the corpus 440 includes selecting content associated with specific sources or types of sources, e.g., specific institutions or individuals viewed as exemplary subject matter experts (SMEs) whose behavior is to be emulated by the QA system. Alternatively, or in addition, the filter criteria may comprise selecting content with desirable results associated with it, e.g., therapy or treatment decisions that resulted in a patient being cured of their diagnosed malady or for which the symptoms were lessened. In addition, other filter criteria may include selecting content that is more contemporary, i.e. content that is within a predetermined window of time of the current date/time, e.g., content that is no older than 2 years old. Each of these filter criteria may be individually utilized or a combination of these filter criteria may be used to select a subset of corpus content for use in generating a training answer key and training cases. Primarily, the time frame and filter may be from when a prescribed actionable event has taken place that was deemed a successful action and a sufficient start time for the domain of that actionable event. The filter restricts corpus content to information within that actionable event time frame.

For example, in some illustrative embodiments, the mechanisms of the illustrative embodiments may be implemented such that the system looks back historically for an actionable event, e.g., a treatment that was recommended. In most cases, the successful outcome of the actionable event, e.g., the treatment, is later in time than the actual event. Thus, the mechanisms of the illustrative embodiments track back within the actionable event time frame to determine when the actionable event occurred, e.g., the treatment was prescribed. The actionable event date may then be tracked back to other related actionable events, e.g., a last diagnosis date or a last previous treatment. Thus, through this back-tracking, an initial start time of the actionable event time frame may be determine to be the first related actionable event and the end time point may be the actionable event time point at which the actionable event leading to the successful outcome occurred, e.g., the start time may be the last diagnosis date and the end time may be the date on which the treatment was prescribed.

The entire corpus 440 may be iteratively processed in this manner to generate training cases and a filtered subset of the corpus.

The filtered subset of the corpus is processed by the answer key and training case generation logic 440 to identify and capture relevant attributes (e.g., symptoms and diagnosis), actions taken (e.g., treatment/therapy prescribed or applied), and date of the actionable event (e.g., date of prescription or application of treatment/therapy). In one illustrative embodiment in which patient medical records are evaluated for treatment information so as to train the QA system to provide treatment recommendations, a key value (e.g., the patient's id) and a reference date are obtained which are associated with a training case. When the illustrative embodiments utilize the training case with the QA system pipeline, all relevant data for that patient id that was available on or before the designated reference date is filtered to generate the filtered subset of the corpus. By capturing just a key to the patient medical records, the mechanisms of the illustrative embodiments are able to alter the definition of data that is relevant over time, e.g., today it may be determined that all that are need are symptoms as extracted features for generating the answer key, but tomorrow it may be realized that family history is also a relevant attribute that should be included in the key question attribute set when submitted to the QA system pipeline.

In some illustrative embodiments, capturing the relevant attributes, analysis of the features of the filtered subset of the corpus (also referred to as a sub-corpus) is performed such that the features within the content in the filtered subset of the corpus may be aggregated. Thus, for example, multiple entries in multiple patient medical records that have similar features and similar dates (e.g., within a predetermined time period of one another) may be considered to represent a similar answer key entry, e.g., multiple medical records referring to the same treatment event at a given point in time for a particular patient or multiple different patient medical records referring to the same symptoms and/or treatments.

Hence, if a first patient, on Jan. 5, 2014 complained of sore throat, runny nose, and fever and was diagnosed with the flu and prescribed Tamiflu, and a second patient on Feb. 21, 2013 complained of a fever and sore throat and was diagnosed with the flu, then these entries may both be considered to represent the same answer key entry, i.e. question features of "sore throat," "runny nose," and "fever" corresponds to a diagnosis of "flu" and a treatment of "Tamiflu." In identifying corresponding entries in the filtered subset of the corpus, the largest set of features may be used, e.g., the features of "runny nose" and "Tamiflu" did not appear in the second patient's entry but because it was present in the first patient's entry, it was included in the features of the answer key entry.

Alternatively, a smallest common set of features may be utilized in which case the answer key entry may comprise the features "sore throat" and "fever" correlated with the diagnosis of "flu" in the above example. The date of the actionable event associated with the aggregated extracted features and action taken may be the most recent date, for example. Thus, in the above example, the Jan. 5, 2014 date would be associated with the aggregate of the extracted features and action taken. In still a further embodiment, a separate set of captured relevant attributes, action taken, and date of actionable event may be generated for each portion of content in the filtered subset of the corpus without performing aggregation.

In short, the key relevant attributes that are extracted when generating training cases and an answer key are those that match the type of answer the QA system is designed to respond with. For example, in one illustrative embodiment, the QA system is designed to return treatment recommendations for medical maladies. Thus, the answer key contains "correct" treatment recommendations which are derived from historical medical records. Thus, when the mechanisms of this illustrative embodiment looks at that historical data, the system of the illustrative embodiment is looking specifically for therapy prescription events (what a doctor prescribed for the patient and when). The date of the therapy decision becomes the reference date and all medical record data in existence at the time of that decision is considered part of the question context.

From the captured relevant attributes, action taken, and date of the actionable events obtained from the content of the filtered subset of the corpus, the answer key and training case generation logic 440 generates answer key entries in an training answer key data structure 470. The answer key entries correlate relevant attributes with the action taken as the correct answer for the relevant attributes. The date of the actionable event provides a historical time context for the answer key entry. Thus, an answer key entry may be of the type:

Symptoms=sore throat, runny nose, fever
Diagnosis=flu
Action=Tamiflu
Date=01.05.14

Thus, during training of the QA system, for a question that has the same or similar symptoms and diagnosis to that of this answer key entry, within a time frame corresponding to the date of 01.05.14, the correct answer that should be generated by a properly operating QA system pipeline is to prescribe Tamiflu.

Thus, the illustrative embodiments provide mechanisms for automatically generating a training answer key and training cases for use in training the QA system pipeline. It should be noted that the entries in the corpus itself represents the knowledge of virtual Subject Matter Experts (SMEs) that is used to create the answer key and training cases. The entries corresponding to the virtual SMEs may be identified by filtering the corpus based on source filter criteria. Entries providing "golden" or correct answers may further be identified by filtering entries in the corpus that resulted in positive results. Moreover, entries in the corpus may be filtered according to temporal characteristics so as to eliminate stale or out of date entries from further use in generating an answer key.

Figure 5:
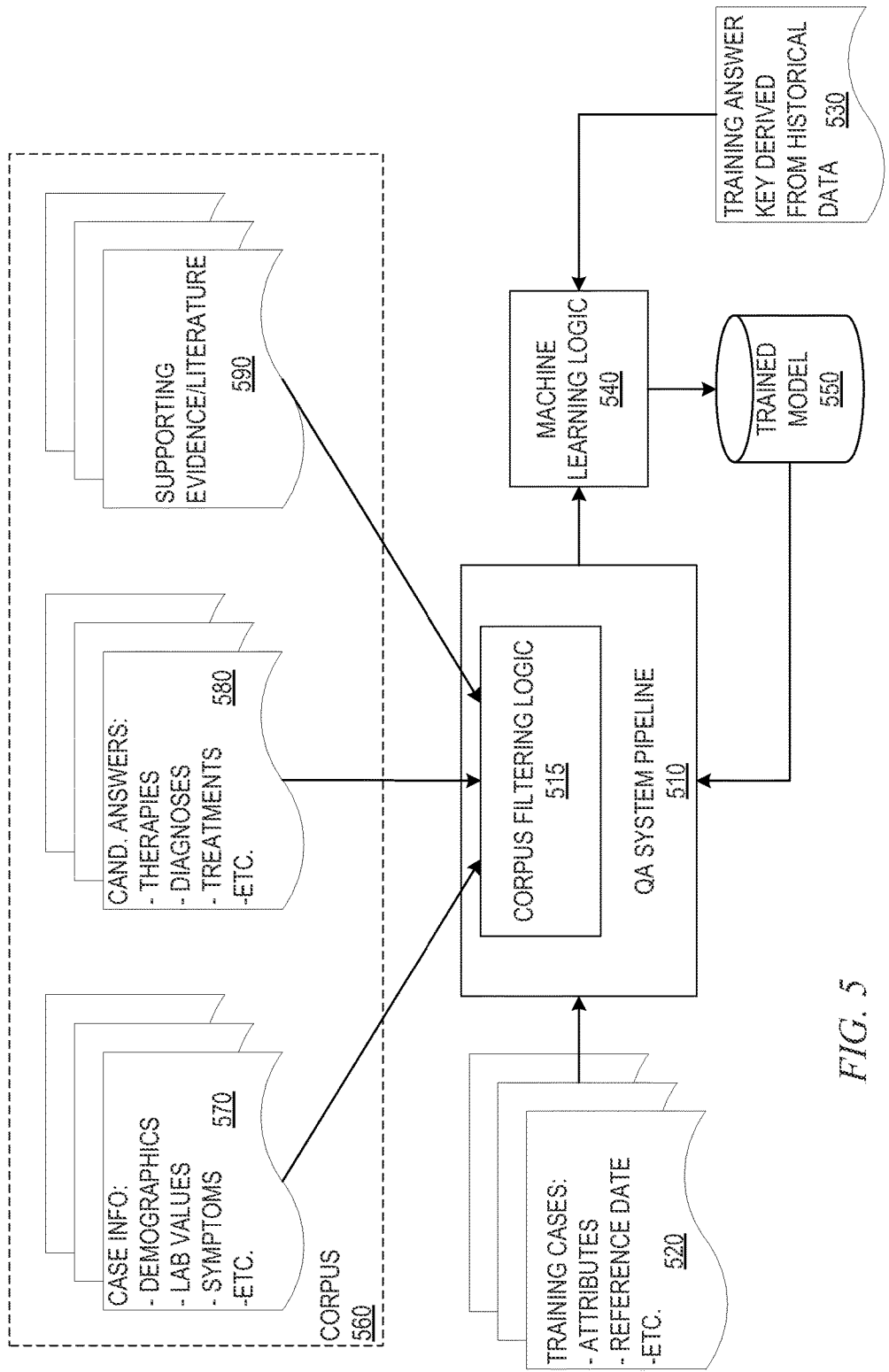
FIG. 5 is an example block diagram illustrating primary operational elements of a machine learning operation for generating trained model using the automatically generated training cases and training answer key in accordance with one illustrative embodiment.

FIG. 5 is an example block diagram illustrating primary operational elements of a machine learning operation for generating trained model using the automatically generated training cases and training answer key in accordance with one illustrative embodiment. As shown in FIG. 5, the elements in the illustrative embodiment operate to train a QA system pipeline 510, which may be a QA system pipeline such as that shown in FIG. 3, for example. In particular, the training of the QA system pipeline 510 involves the evaluation of results generated by the QA system pipeline 510 by machine learning logic 540, in response to the submission of training cases 520 and based on the training answer key 530, to generate the trained model 550. The QA system pipeline 510 operates on a corpus of information 560, which may be the same corpus of information used to generate the training cases 520 and answer key 530, but prior to filtering and selection of the sub-corpus used to generate the answer key 530. The corpus of information 560 may comprise, for example, case information 570, candidate answer information 580, and supporting evidence/literature 590, each of which may be provided in a structured or unstructured (natural language) manner. In one illustrative embodiment, the information 570-590 in the corpus 560 is only the information determined to be from a source that is credible and reliable according to the filter criteria specified when using the corpus 560 to generate the answer key 530. Thus, the corpus 560, if processed properly by the QA system pipeline 510, should return the same answers as specified in the answer key 530 since the corpus 560 comprises the information used to generate the answer key 530.

While FIG. 5 shows these portions of information 570-590 being separate entities within the corpus 560 for purposes of discussion, in actuality this information is combined together within the corpus such that analysis of the corpus 560 is necessary to extract the various information elements. That is, in one illustrative embodiment, the corpus 560 may comprise patient medical records and healthcare and medical resources, texts, publications and other literature. The patient medical records may have entries that provide both the case information and the candidate answers 570 and 580 combined together in structured or natural language formats. Thus, the patient medical record may comprise a plurality of structured fields for specifying the patient's name, date of birth, address, occupation, contact information, answers to health status questionnaire, and other standard information used to identify the patient and identify a condition of the patient. In addition, the patient medical record may comprise free-form text areas where notes may be included in the patient medical record by medical professionals, e.g., nurses, doctors, medical technicians, lab personnel, and the like, in a natural language manner. Thus, as mentioned above, a natural language note regarding care of the patient of the type "Jan. 5, 2014: Patient complains of sore throat, runny nose, and fever. Diagnosed patient with the flu and prescribed Tamiflu. Doctor Johnathan Smith" may be included in the patient medical record. Such natural language text may be periodically added to the patient medical record with each subsequent session in which the patient obtains care from a medical professional.

Through analysis of the corpus 560, the information in the corpus may be parsed and annotated such that the separate portions of information 570-590 are identified. Thus, for example, the case information 570 may be identified and may include such information as demographics, laboratory results, symptoms, and the like. The candidate answer information 580 may comprise therapies, treatments, diagnoses, and the like, identified in the patient medical records. The case information 570 may be correlated with the candidate answers such that a match of a set of information in the case information 570 may be used to identify a corresponding candidate answer in the candidate answer information 580. The corpus of supporting evidence and literature 590 may be other information that is present in medical resources (Prescription Drug Reference Manuals and the like), medical journals, treatment and therapy documentation, and the like, that may be used by the QA system pipeline 510 when evaluating evidence in support of the candidate answers so as to score the confidence of the candidate answers.

The QA system pipeline 510, in accordance with the illustrative embodiments, implements a corpus filtering engine 515 that operates on the information in the corpus to filter the corpus 560 according to a reference temporal characteristic associated with the particular training case 520 being evaluated. That is, as shown in FIG. 5, the training cases 520 each have a set of attributes or features (question features) and an associated reference temporal characteristic, e.g., date. The attributes or features, in the context of a medical treatment recommendation QA system pipeline, represent features similar to the case information 570 for a particular patient, e.g., age, gender, laboratory result values, symptoms, and the like. The reference temporal characteristic (reference date) provides a historical context for the training case attributes or features, e.g., the patient complained of a stomach ache on Mar. 12, 2013. As discussed above, these features and reference date may be automatically generated from the automatic training case generation operation above which identifies the features and reference date from analysis of actual patient medical records in the corpus 560 or a training corpus different from corpus 560. Thus, by matching attributes of the training case 520 to features in the case information, a corresponding candidate answer 580 for the training case 520 may be generated and supporting evidence/literature 590 may be used to generate a confidence score associated with the candidate answer based support for the candidate answer in the supporting evidence/literature 590.

The reference date associated with the training case 520 is read by the corpus filtering engine 515 which filters the information in the corpus 560 based on the specified reference date, such that only information in the corpus 560 that is associated with a date that is on or before the reference date is considered by the QA system pipeline 510 when generating candidate answers for the training case. Thus, for example, if a patient medical record had one entry that was from February 2007 and another entry that was from March 2012, if the reference date is January 2010, then the entry from March 2012 would not be considered for generation of a candidate answer to the training case since the information present in the entry from March 2012 would not have been known at the time of the training case. Thus, the corpus of information 560 may comprise a larger set of information than is used to generate candidate answers for any one particular training case.

Based on the filtered corpus of information generated by the corpus filtering engine 515, the QA system pipeline 510 operates on the filtered corpus of information in much the same manner as already described above with regard to FIG. 3 so as to generate one or more candidate answers for the training case, and corresponding confidence scores for the candidate answers. In generating the confidence scoring of the candidate answers by annotators in the QA system pipeline, the QA system pipeline 510 utilizes the trained model 550 to provide statistical measures or weights to be applied by the various annotators to the features and candidate answers to thereby generate the confidence score for the candidate answer, or to be applied to the results generated by the various annotators when generating the confidence score for the candidate answer. Thus, for example, a first annotator's results may be weighted relatively highly while a second annotator's results may be weighted relatively lowly such that the relative influence on the final confidence scoring of the candidate answers is adjustable.

The resulting candidate answers and corresponding confidence score information is output to the machine learning logic 540 which operates to compare the candidate answers with the training answer key 530 to determine if the QA system pipeline 510 generated the correct answer and if so, if the correct answer was scored appropriate so as to have the correct answer output as the answer to the particular training case with a sufficient level of confidence. The machine learning logic 540 may then, based on any discrepancies between the candidate answers and scores with the correct answers in the answer key 530, modify weight values or the like in the trained model 550 so as to modify the scoring of candidate answers by the QA system pipeline 510.

The trained model is a statistical model reflecting how various answer scoring algorithms, i.e. annotators, employed within the QA system pipeline 510 should be weighted to yield optimal results/accuracy based on the set of training cases used for training The trained model is used by the QA system pipeline 510 during training and at runtime to evaluate cases (training or new cases) presented to the QA system pipeline. During training, the trained model 550 is not actually "trained" as of yet, but is continuously modified as needed depending upon the results generated by the QA system pipeline 510 in response to the submission of training cases 520. Once the machine learning logic 540 determines that the QA system pipeline 510 is outputting candidate answers and corresponding confidence scores that are within an acceptable tolerance of the correct answers and confidence scores specified by the training answer key 530, the training may be discontinued and the then existing trained model 550 may be used as the final trained model 550 for the QA system pipeline 510 to be used during runtime operation.

During runtime, the trained model has been trained using the training cases and training answer key automatically generated by the mechanism of the illustrative embodiments and represents the then determined optimal weights to be applied to the annotators (or scoring algorithms) of the QA system pipeline 510. Candidate answers for new cases are evaluated by first running the QA system pipeline 510 answer scoring algorithms (annotators) and then applying the weighting factors from the machine learning-derived trained model 550 to yield an overall confidence level for each candidate answer. This may be done, for example, during the hypothesis and evidence scoring stage 350 in FIG. 3, for example. Thus, the trained model 540 is generated while the QA system pipeline 510 is operated in a special "training" mode using the automatically generated training cases 520 and training answer key 530 to produce a trained, machine learning-based trained model 540 that is then used with the same QA system pipeline 510 when it is operating in a non-training runtime mode, i.e. during runtime.

During runtime, it should be appreciated that a larger corpus 560, encompassing information not present in the corpus used to perform training, may be utilized and the cases presented to the QA system pipeline 510 as input questions will be different from the training cases 520. Moreover, the answer key 530 and corpus filtering engine 515 are not used during runtime operation. In essence, during runtime operation, the QA system pipeline 510 operates as described above with regard to FIG. 3 with the only difference being that the QA system pipeline 510 uses the trained model 550, generated by the training of the illustrative embodiments, to apply weights to the annotators (or scoring algorithms) for purposes of candidate answer scoring and ultimately candidate answer and final answer selection.

It should be noted that while the illustrative embodiments have been described as filtering the corpus 560 using the corpus filtering engine 515 prior to the operation of the QA system pipeline on the filtered information to generate candidate answers, the illustrative embodiments are not limited to such. Rather, the filtering can be performed as a later stage in the QA system pipeline 510 by processing the entirety of the corpus 560 and then filtering out candidate answers associated with dates that are not on or before the reference date. Thus, the QA system pipeline 510 may operate much the same as it generally does as shown in FIG. 3, but with a filtering stage added, or implemented in the synthesis stage 360, final confidence merging and ranking stage 370, or the like, for example, to filter out candidate answers that are based on information not available within the historical context of the training case specified by the reference date.

Figure 6:
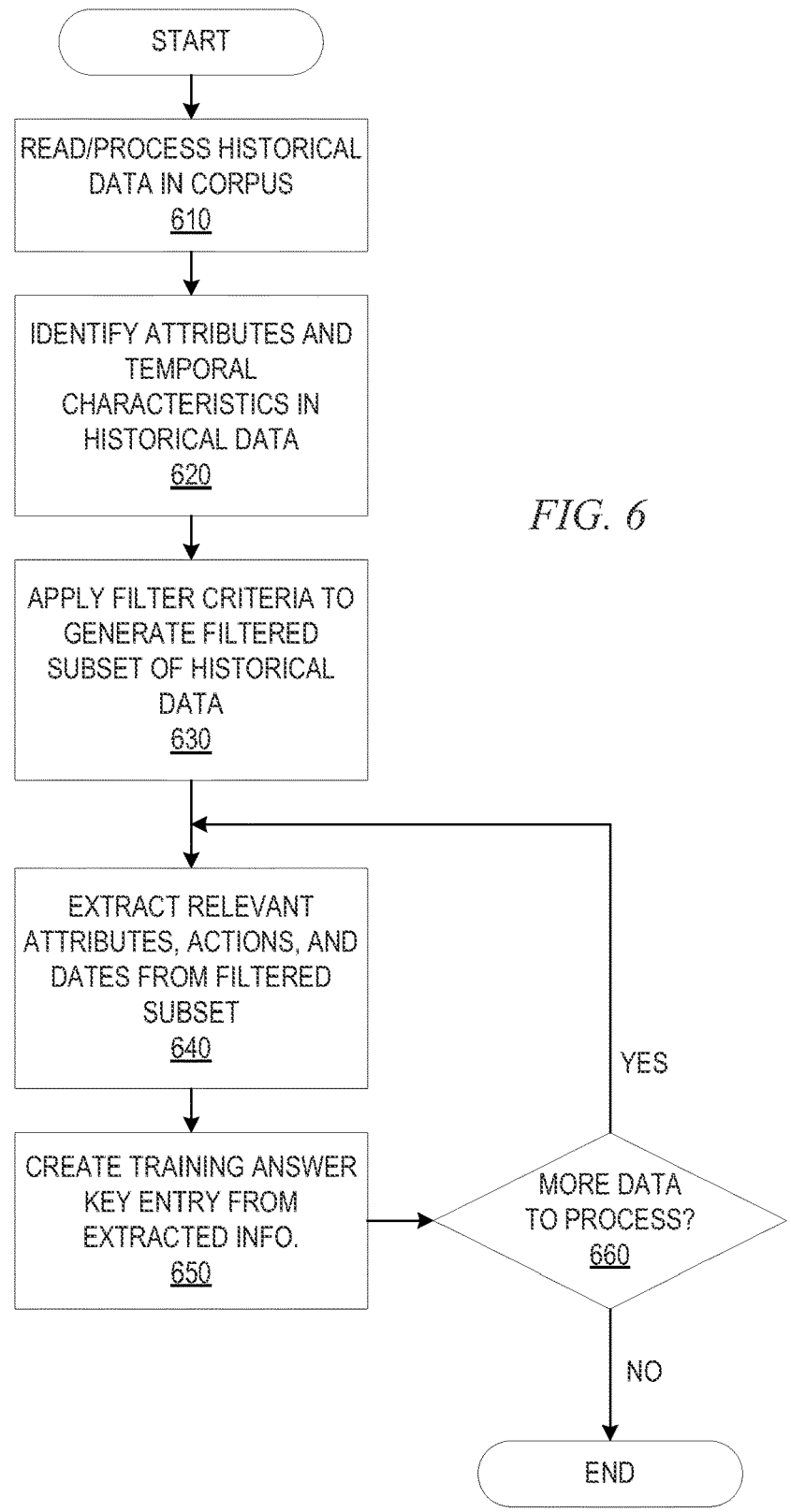
FIG. 6 is a flowchart outlining an example operation of a training engine for automatically generating training cases and a training answer key in accordance with one illustrative embodiment.

FIG. 6 is a flowchart outlining an example operation of a training engine for automatically generating training cases and a training answer key in accordance with one illustrative embodiment. As shown in FIG. 6, the operation starts by reading and processing historical data in a corpus of information (step 610). Through processing of the historical data, features or attributes, and temporal characteristics associated with the features or attributes, are identified and used to generate one or more training cases (step 620).

One or more filter criteria are applied to the historical data based on training objectives (e.g., source filtering, results filtering, time frame filtering, etc.) so as to generate a filtered subset of the historical data (step 630). Relevant attributes, actions taken, and dates of actionable event are extracted from the filtered subset of historical data (step 640). The correlation of relevant attributes with the action taken and the date of the actionable event is then used to create a new training answer key entry with the correct answer for that answer key entry being the action taken (step 650). The operation then determines if there is any more filtered historical data to be processed (step 660). If so, the operation returns to step 640 and additional relevant attributes, actions taken, and dates of actionable events are extracted and used to generate additional answer key entries. If there is no more filtered historical data to process, the operation terminates.

Figure 7:
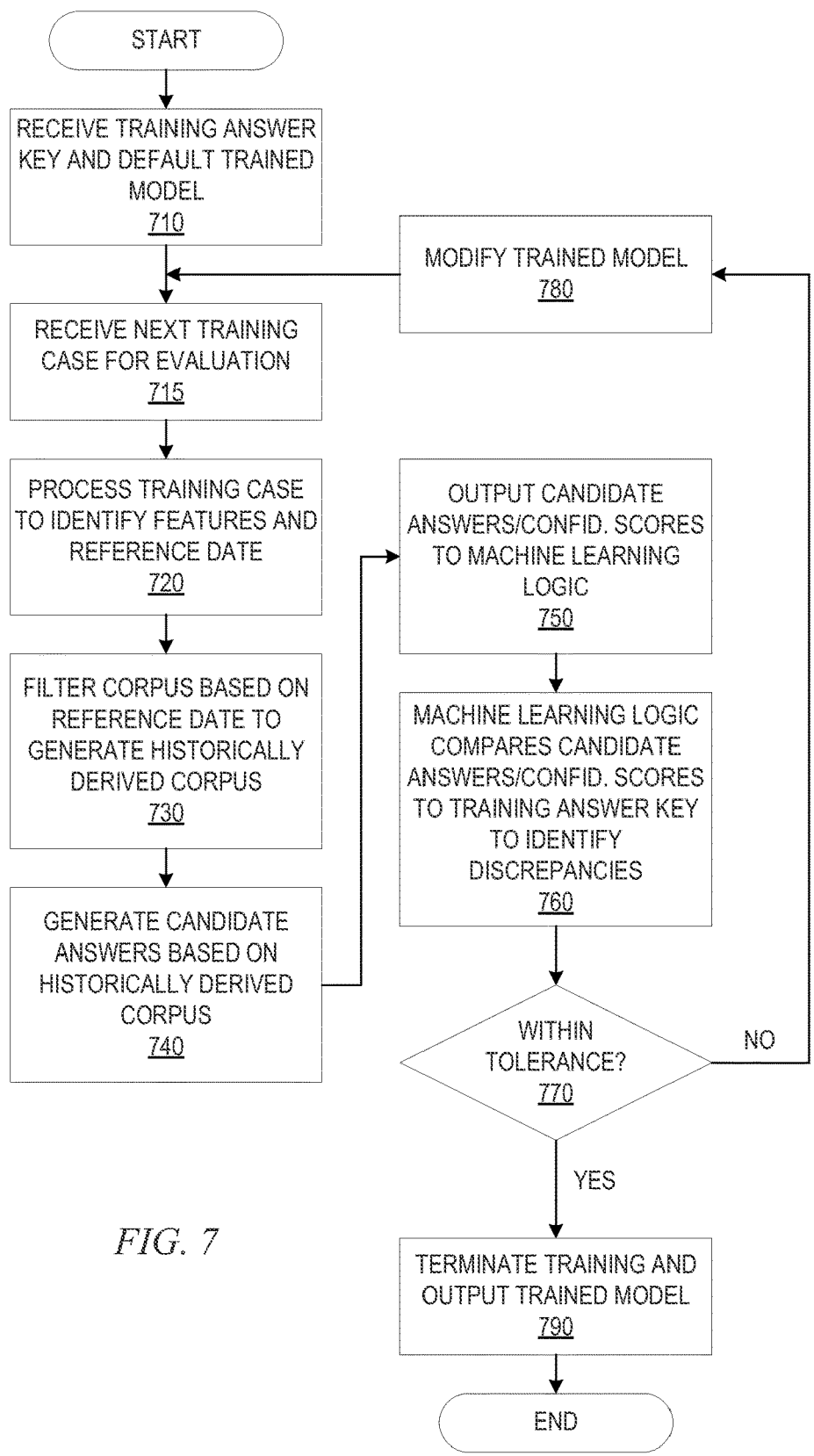
FIG. 7 is a flowchart outlining an example operation for training a QA system pipeline in accordance with one illustrative embodiment.

FIG. 7 is a flowchart outlining an example operation for training a QA system pipeline in accordance with one illustrative embodiment. As shown in FIG. 7, the operation starts by receiving, in the QA system pipeline, a training answer key and default trained model (step 710). The QA system pipeline also receives a next training case for evaluation as part of the training operation (step 715). The training case and training answer key are automatically generated using the operation outlined in FIG. 6 in accordance with one or more of the illustrative embodiments previously described above. The default trained model may be a statistical model of weights to be applied to annotators or scoring algorithms of the QA system pipeline that is initialized with a set of default weight values, is set at a previously generated setting of weights based on a previous training of the QA system pipeline, or the like.

The QA system pipeline processes the training case by parsing it, extracting features of the training case, and identifying a reference date associated with the training case (step 720). The reference date is used by corpus filtering logic of the QA system pipeline to filter out content of the corpus that has associated dates that do not fall within a historical context specified by the reference date and thereby generate a historically derived corpus upon which the QA system pipeline will operate (step 730). The QA system pipeline then processes the historically derived corpus based on the extracted features from the training case to generate one or more candidate answers and corresponding confidence scores for the candidate answers (step 740).

The candidate answers and individual answer scores generated by the QA system pipeline for the training case based on the historically derived corpus are output to machine learning logic (step 750). That is, input to the machine learning process comprises results produced by the QA system pipeline for all cases used for training purposes where, for each candidate answer, the score of each answer scoring algorithm utilized in the QA system pipeline is captured. These are typically referred to as scoring features. Thus, for each candidate answer, there is a vector/list of scoring features produced by the algorithms in the QA system pipeline. This training output is further annotated, using the answer key as input to designate each candidate answer as correct or incorrect. This set of scoring features and correct/incorrect attributes are fed into a statistical modelling package and, using standard statistical techniques, such as logistic regression, a model is produced which weighs each scoring feature in such a way as to maximize the number of correct candidate answers that are assigned the highest confidence score.

The machine learning logic compares the candidate answers and confidence scores to correct answers specified in the training answer key to identify any discrepancies (step 760). A determination is made as to whether the discrepancies, if any, are within a configured acceptable tolerance value (step 770). If not, the trained model is modified so as to modify appropriate weight values within the trained model to thereby affect the operation of the QA system pipeline when scoring, ranking, and selecting candidate answers (step 780). The operation then returns to step 715 with a next training case being received for processing. If the discrepancies are within the configured acceptable tolerance, the training operation is terminated and the current state of the trained model is output for use during runtime operation of the QA system pipeline (step 790).

Thus, the illustrative embodiments provide mechanisms for automatically generating training cases and a training answer key based on historical data in a corpus of information. Temporal characteristics are associated with the training cases and entries in the training answer key so as to facilitate proper training of a QA system pipeline taking into consideration the historical context of the training case, answer key, and information available in the training corpus. When processing the training cases using the QA system pipeline, corpus filtering logic is implemented to filter the corpus based on the temporal characteristic of the training case so that only the information in the corpus that would have been available within the historical context specified by the temporal characteristic is considered when generating candidate answers to the training case. Based on machine learning logic operating on the generated candidate answers to the training case and the training answer key, a model is trained with appropriate statistical measures or weights to be applied to, or by, the annotators or scoring algorithms implemented within the QA system pipeline.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system having a processor and a memory, wherein the memory comprises instructions which are executed by the processor to cause the processor to implement a training engine for generating training cases and an answer key from a historical corpus for training a Question and Answer (QA) system, the method comprising:

receiving, by corpus ingestion logic executing within the training engine, a corpus of information comprising historical data;

automatically applying, by filtering logic executing within the training engine, one or more filter criteria to the historical data to extract filtered historical data relevant to a training objective for training the QA system pipeline;

automatically capturing, by answer key and training case generation logic executing within the training engine, attribute data, action data, and temporal characteristic data from the filtered historical data;

automatically generating, by the answer key and training case generation logic, an answer key entry in an automatically generated training answer key data structure based on the attribute data, action data, and temporal characteristic data, wherein the action data of the answer key entry specifies a correct answer to a question, the attribute data of the answer key entry comprises question features for correlating the question to the correct answer, and the temporal characteristic data specifies a historical date or time at which the answer was considered correct for the question; and training, by the training engine, a QA system pipeline for the QA system using the automatically generated training answer key data structure at least by, for each training question processed by the QA system pipeline and having a corresponding correct answer in the training answer key data structure, selecting a subset of information in the corpus of information, wherein the subset of information comprises information having an associated temporal characteristic that is contemporaneous with or historically prior to the temporal characteristic data of the correct answer to the training question, and training the QA system pipeline using the selected subset of information.

2. The method of claim 1, wherein a correct answer associated with the answer key entry is an action specified by the action data, and wherein the temporal characteristic data provides a historical context for the answer key entry.

3. The method of claim 1, wherein the one or more filter criteria comprises at least one of a source filter criterion used to select historical data associated with specific sources of information in the corpus of information, a temporal filter criterion that is used to select information in the corpus of information that is more contemporary, or a confidence filter criterion that is used to select historical data with at least a specified level of confidence associated with the historical data.

4. The method of claim 1, wherein training the QA system pipeline using the automatically generated training answer key data structure comprises:

receiving, by the QA system pipeline, a training case comprising a training question for processing by the QA system pipeline and a training case temporal characteristic;

filtering, by the QA system pipeline, the corpus of information based on the training case temporal characteristic to thereby generate a temporally filtered sub-corpus; and processing, by the QA system pipeline, the training question based on the temporally filtered sub-corpus to generate an answer to the training question.

5. The method of claim 4, wherein training the QA system pipeline further comprises:

comparing, by the QA system pipeline, the answer to the training question with a correct answer in a corresponding training answer key entry of the training answer key data structure; and modifying, by the QA system pipeline, an operation of the QA system pipeline based on results of the comparing.

6. The method of claim 5, wherein the corresponding training answer key entry of the training answer key data structure is a training answer key entry having attributes matching attributes of the training question and a temporal characteristic matching the training case temporal characteristic.

7. The method of claim 4, wherein training the QA system pipeline comprises generating, through a machine learning process, a trained model, having weights to be applied to annotation logic of the QA system pipeline, based on a degree of correspondence between the answer to the training question and a correct answer specified in a training answer key entry corresponding to the training question and training case temporal characteristic of the training case.

8. The method of claim 1, wherein the corpus of information comprises financial investment information, and wherein the filtered historical data comprises entries in the financial investment information directed to investment decisions made by financial investors on or prior to a date or time specified in the temporal characteristic.

9. The method of claim 1, wherein the corpus of information comprises patient medical records, and wherein the filtered historical data comprises entries in patient medical records directed to healthcare services provided to patients on or prior to a date or time specified in the temporal characteristic.

10. A computer program product comprising a computer readable storage medium having a computer readable program stored therein, wherein the computer readable program, when executed on a computing device, causes the computing device to implement a training engine for generating training cases and an answer key from a historical corpus for training a Question and Answer (QA) system, wherein the computer readable program further causes the computing device to:

receive, by corpus ingestion logic executing within the training engine, a corpus of information comprising historical data;

automatically apply, by filtering logic executing within the training engine, one or more filter criteria to the historical data to extract filtered historical data relevant to a training objective for training a Question and Answer (QA) system pipeline;

automatically capture, by answer key and training case generation logic executing within the training engine, attribute data, action data, and temporal characteristic data from the filtered historical data;

automatically generate, by the answer key and training case generation logic, an answer key entry in an automatically generated training answer key data structure based on the attribute data, action data, and temporal characteristic data, wherein the action data of the answer key entry specifies a correct answer to a question, the attribute data of the answer key entry comprises question features for correlating the question to the correct answer, and the temporal characteristic data specifies a historical date or time at which the answer was considered correct for the question; and train, by the training engine, a QA system pipeline for the QA system using the automatically generated training answer key data structure at least by, for each training question processed by the QA system pipeline and having a corresponding correct answer in the training answer key data structure, selecting a subset of information in the corpus of information, wherein the subset of information comprises information having an associated temporal characteristic that is contemporaneous with or historically prior to the temporal characteristic data of the correct answer to the training question, and training the OA system pipeline using the selected subset of information.

11. The computer program product of claim 10, wherein a correct answer associated with the answer key entry is an action specified by the action data, and wherein the temporal characteristic data provides a historical context for the answer key entry.

12. The computer program product of claim 10, wherein the one or more filter criteria comprises at least one of a source filter criterion used to select historical data associated with specific sources of information in the corpus of information, a temporal filter criterion that is used to select information in the corpus of information that is more contemporary, or a confidence filter criterion that is used to select historical data with at least a specified level of confidence associated with the historical data.

13. The computer program product of claim 10, wherein the computer readable program further causes the computing device to train the QA system pipeline using the automatically generated training answer key data structure at least by:
receiving, by the QA system pipeline, a training case comprising a training question for processing by the QA system pipeline and a training case temporal characteristic;
filtering, by the QA system pipeline, the corpus of information based on the training case temporal characteristic to thereby generate a temporally filtered sub-corpus; and
processing, by the QA system pipeline, the training question based on the temporally filtered sub-corpus to generate an answer to the training question.

14. The computer program product of claim 13, wherein the computer readable program further causes the computing device to train the QA system pipeline at least by:
comparing, by the QA system pipeline, the answer to the training question with a correct answer in a corresponding training answer key entry of the training answer key data structure; and
modifying, by the QA system pipeline, an operation of the QA system pipeline based on results of the comparing.

15. The computer program product of claim 14, wherein the corresponding training answer key entry of the training answer key data structure is a training answer key entry having attributes matching attributes of the training question and a temporal characteristic matching the training case temporal characteristic.

16. The computer program product of claim 13, wherein the computer readable program further causes the computing device to train the QA system pipeline at least by generating, through a machine learning process, a trained model, having weights to be applied to annotation logic of the QA system pipeline, based on a degree of correspondence between the answer to the training question and a correct answer specified in a training answer key entry corresponding to the training question and training case temporal characteristic of the training case.

17. The computer program product of claim 10, wherein the corpus of information comprises patient medical records, and wherein the filtered historical data comprises entries in patient medical records directed to healthcare services provided to patients on or prior to a date or time specified in the temporal characteristic.

18. An apparatus comprising:
a processor; and
a memory coupled to the processor, wherein the memory comprises instructions which, when executed by the processor, cause the processor to implement a training engine for generating training cases and an answer key from a historical corpus for training a Question and Answer (QA) system, wherein the instructions cause the processor to:
receive, by corpus ingestion logic executing within the training engine, a corpus of information comprising historical data;
automatically apply, by filtering logic executing within the training engine, one or more filter criteria to the historical data to extract filtered historical data relevant to a training objective for training a Question and Answer (QA) system pipeline;
automatically capture, by answer key and training case generation logic executing within the training engine, attribute data, action data, and temporal characteristic data from the filtered historical data;
automatically generate, by the answer key and training case generation logic, an answer key entry in an automatically generated training answer key data structure based on the attribute data, action data, and temporal characteristic data, wherein the action data of the answer key entry specifies a correct answer to a question, the attribute data of the answer key entry comprises question features for correlating the question to the correct answer, and the temporal characteristic data specifies a historical date or time at which the answer was considered correct for the question; and
train, by the training engine, a QA system pipeline for the QA system using the automatically generated training answer key data structure at least by, for each training question processed by the QA system pipeline and having a corresponding correct answer in the training answer key data structure, selecting a subset of information in the corpus of information, wherein the subset of information comprises information having an associated temporal characteristic that is contemporaneous with or historically prior to the temporal characteristic data of the correct answer to the training question, and training the OA system pipeline using the selected subset of information.

19. The apparatus of claim 18, wherein training the QA system pipeline using the automatically generated training answer key data structure comprises:
receiving, by the QA system pipeline, a training case comprising a training question for processing by the QA system pipeline and a training case temporal characteristic;
filtering, by the QA system pipeline, the corpus of information based on the training case temporal characteristic to thereby generate a temporally filtered sub-corpus; and
processing, by the QA system pipeline, the training question based on the temporally filtered sub-corpus to generate an answer to the training question.

20. The apparatus of claim 19, wherein training the QA system pipeline further comprises:
comparing, by the QA system pipeline, the answer to the training question with a correct answer in a corresponding training answer key entry of the training answer key data structure; and
modifying, by the QA system pipeline, an operation of the QA system pipeline based on results of the comparing, wherein the corresponding training answer key entry of the training answer key data structure is a training answer key entry having attributes matching attributes of the training question and a temporal characteristic matching the training case temporal characteristic.

\* \* \* \* \*